United States Patent [19]

Meinhardt et al.

[11] Patent Number: 5,149,535
[45] Date of Patent: Sep. 22, 1992

[54] PROCESS FOR THE MODIFICATION OF WHEY

[76] Inventors: Horst Meinhardt, Rheinstrasse 16, 5419 Herschbach; Ulrich Leithe, Tuebinger Strasse 31, 4000 Duesseldorf, both of Fed. Rep. of Germany

[21] Appl. No.: 395,317

[22] Filed: Aug. 17, 1989

[30] Foreign Application Priority Data

Aug. 17, 1988 [DE] Fed. Rep. of Germany ....... 3827833

[51] Int. Cl.⁵ .................. A61K 35/78; A61K 9/00
[52] U.S. Cl. ................. 424/195.1; 424/43; 424/583
[58] Field of Search ............ 424/195.1, 43, 583

[56] References Cited

U.S. PATENT DOCUMENTS 4,837,035  6/1989  Baker et al. .................. 426/43
4,970,083  11/1990  Akahoshi et al. ............. 426/34

FOREIGN PATENT DOCUMENTS 2819940  2/1980  Fed. Rep. of Germany .

OTHER PUBLICATIONS

Bergey's Manual of Determinative Bacteriology.

Primary Examiner—John W. Rollins
Attorney, Agent, or Firm—Hill, Van Santen, Steadman & Simpson

[57] ABSTRACT

Method for the manufacture of modified whey with the assistance of lactic acid bacteria for use in manufacturing washing-active substances, as well as, cosmetic and pharmaceutical products, including the step of at least partially freeing the way of lactose by utilizing suitable lactic acid bacteria on the basis of fermentation.

11 Claims, No Drawings

PROCESS FOR THE MODIFICATION OF WHEY

BACKGROUND OF THE INVENTION

The present invention relates to a method for producing modified whey, utilizing lactic acid bacteria, for use in the manufacture of washing-active substances, as well as cosmetic and pharmaceutical products.

German Pat. No. 28 19 940 discloses a method for manufacturing washing-active substances based on whey (also referred to as milk serum) utilizing lactic acid rods. In the method set forth in the German Patent, sugar-containing compounds are added to the whey, and the resultant solution is subjected to a three-stage fermentation. The process, however, requires very involved control of the process making the method correspondingly cost-intensive and work-intensive.

SUMMARY OF THE INVENTION

The present invention provides a method that retains all the advantages of the prior method, but provides a simple and more cost-effective process control, while at the same time expanding the fields of possible application for the modified whey product.

To this end, a method is provided for manufacturing modified whey, utilizing lactic acid bacteria, for use in manufacturing washing-active substances, cosmetics, and pharmaceutical products. Pursuant to the method of the present invention, the whey is at least partially freed of lactose with suitable lactic acid bacteria on the basis of fermentation.

In an embodiment of the present invention, the lactic acid bacteria is chosen from the group consisting of *Lactobacillus acidophilus, Lactobacillus bulgaris, Lactobacillus lactis, Lactobacillus helveticus, Lactobacillus casei, Streptococcus lactis,* and *Streptococcus thermophilus.*

In an embodiment of the present invention, the whey is inoculated with at least one lactic acid bacterium phylum either before or during the fermentation.

In an embodiment of the present invention, the duration of the fermentation process is selected such that the lactose is completely broken down to a great degree.

In an embodiment of the present invention, medicinal herbs or botanical constituents or extracts thereof are added to the whey before the fermentation step.

In an embodiment of the method of the present invention, modified whey is concentrated by drying, vacuum drying, or freeze drying or is pulverized or drawn off under a $CO_2$ excess.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for the manufacture of modified whey, with the assistance of lactic acid bacteria, for use in manufacturing active washing substances, cosmetics, and pharmaceuticals. Pursuant to the method, the whey is at least partially liberated of lactose by a suitable lactic acid bacteria on the basis of fermentation. It has been found to be especially advantageous when the lactic acid bacteria is chosen from the group consisting of *Lactobacillus acidophilus, Lactobacillus bulgaris, Lactobacillus lactis, Lactobacillus helveticus, Lactobacillus casei, Streptococcus lactis,* and *Streptococcus thermophilus.*

The inventors of the present invention have surprisingly found that the method of the present invention, which is much simpler than the prior method for manufacturing washing-active substances provides a resultant product that has all the advantageous properties produced by the prior method. Accordingly, the use, manipulation, and storing, of the whey is ensured without destroying its biological activity. Furthermore, the whey produced pursuant to the method of the present invention, maintains its physiological and qualitative advantages as a valuable raw material.

Accordingly, the quality of the product manufactured by the method of the present invention is at least equivalent in every manner to the products manufactured according to the prior, three-stage method and can be utilized in all forms of application cited therein. Additionally, the method of the present invention also allows the modified whey to be utilized in other areas of application, such as, for example, cosmetics and pharmaceutics.

The method of the present invention plays a significant role in that the combination of the active ingredients of the inventively manufactured whey and, thus, of the final product to be manufactured therefrom, is defined by the parameters and type of bacteria, control of the fermentation temperature, and duration of the fermentation process. Utilizing the method of the present invention, whey-based active ingredient combinations, having different advantageous active mechanisms for specific applications can be created.

In order to use the whey in various applications, it is necessary, to more or less, rid the whey of lactose by fermentation with a suitable bacteria and to create a natural, specific milieu for the use of the whey. This effect is produced by various types of lactic acid bacterium that can include, for example, lactobacillus acidophilus, *Lactobacillus bulgaris, Lactobacillus lactis, Lactobacillus helveticus, Lactobacillus casei, Streptococcus lactis,* and *Streptococcus thermophilus.* However, it should be noted that other types of lactic acid bacterium can be used in the method of the present invention. For example, the bacteria can already be present in the whey, from cheese production. For example, *Lactobacillus casei* and/or *Streptococcus thermophilus* can be utilized by a suitable control of the fermentation temperature, without the further addition of a fresh bacteria culture.

Over and above this, however, it is necessary in some specific applications to inoculate the whey with bacterium phylus (or phyla), that are most suitable for the end use of the whey, before or during the fermentation step. In this regard, a great variety of combinations are possible.

For example, the lactic acid bacteria such as, for instance, *Streptococcus thermophilus,* that are already present in the whey can be used in the beginning of the fermentation step or the initiation of fermentation process can be achieved by inoculation with a corresponding bacterium phylum. The change in the milieu that is thereby achieved in the whey, creates optimum growth conditions for further lactic acid bacteria, for example lactobacilli, under certain conditions that are required to achieve the product milieu, and are therefore added at a later point during the fermentation process. Depending on the specific application, homofermentative and/or heterofermentative lactic acid bacteria can be used for this purpose. These form respectively different product milieus that satisfy specific milieu conditions and demands.

Predominantly L(+), D(−) or DL lactic acid is formed by the use and through the utilization of, homofermentative lactic acid bacteria. This creates a milieu that is particularly gentle on the skin, mucous membrane and body. Such a homofermentative lactic acid bacteria, for example, is *Lactobacillus acidophilus.*

By utilizing heterofermentative lactic acid bacteria such as, for example, lactobacillus lactis, acetic acid and other metabolic products (flavorings, enzymes, citric acid) are formed in addition to lactic acid. The formation of these products makes such a milieu suitable particularly for applications for manufacturing washing-active substances.

However, due to the breakdown of lactose, the formation of lactic acid, and the elimination of $CO_2$, all lactic acid bacteria, including lactic acid streptococci create a stable lactate milieu that is suitable for these areas of application and additionally other areas of use such as those discussed below. Over and above this, a specific active ingredient characteristic can also be achieved by controlling the fermentation temperature and duration of the fermentation process.

The method of the present invention can be implemented in suitable containers or tank systems. The process temperature is chosen so that it is optimum considering the respective species of lactic acid bacterium. The process temperature, for example, in the case of *Lactobacillus acidophilus,* is approximately 37° C. It should be noted, that the process temperature can vary upwardly or downwardly given a different bacteria phyla.

After the optimum process temperature has been achieved, to which end cooling or heating must be performed under certain conditions, the whey is then subjected to the fermentation. The corresponding fermentation process is then discontinued after the desired degree of lactose breakdown has been achieved. Due to the simultaneous elimination of carbon dioxide, the complete breakdown of the lactose can be easily identified as when the development of gas has ended.

The fermented whey, or products manufactured therefrom, can be concentrated or pulverized by drying, vacuum drying or freeze drying for better storage or further-processing. For example, the whey produced according to the method of the present invention can be concentrated to about 1/10 of its initial weight by vacuum drying. The whey will then be present as a viscous mass that can be further-processed as a preliminary product and thus enables higher active ingredient concentration of existing amino acids and other valuable components in the final product.

Particularly in those applications wherein a corresponding pre-concentration of the product is not desirable, packaging and storing under excess $CO_2$ is recommendable since milieu-suited conditions are thereby involved.

The whey manufactured according to the method of the present invention has a controlled, stable, lactate biological milieu and, after complete fermentation, is free of lactose that is problematical for some applications. By way of example, and not limitation, examples of the present invention will now be set forth. The examples demonstrate the versatility of use of the resultant product.

EXAMPLE 1

Whey produced during the production of cheese was immediately filled into fermentation tanks. The temperature of the whey was approximately 30° C. The pH value of the fresh whey was approximately 5.8 and the lactose content was approximately 4.7%. The whey was first laced with a substrate inoculated with *Lactobacillus acidophilus* from a pure culture. The tanks were then closed in an air-tight manner with fermentation heads, and a fermentation temperature of 30° C. was maintained. The duration of the fermentation step was 25 days.

After 25 days, the modified whey created had a pH value of approximately 3.4 and a lactose content of approximately 0.35% and had a pronounced lactate milieu with a large population of lactic acid bacteria lactobacillus acidophilus. The modified whey was then utilized in the production of body cleansing products.

EXAMPLE 2

Whey produced pursuant to the method of the present invention with *Lactobacillus lactis* or lactic acid streptococci, such as *Streptococcus lactis* and *Streptococcus thermophilus,* can be directly used as an acidic cleaning product or as an initial material for the manufacture of cleaning agents such as, for example, rinses, all-purpose cleaners, household and industrial cleaners, as well as detergents. When the modified whey is compounded with surface-active substances such as, for example, fatty alcohol sulphates, fatty alcohol ether sulphates, fatty alcohol polyglycol ethers based on of linear, vegetable fats and oils, protein fatty acid condensates, cocobetaines, etc. then particular washing-active complexes arise. The milieu-suited, washing-active substances that are created are particularly well-suited both for the biological requirements of man as well as the environment.

It has been demonstrated that products produced by the method of the present invention do not produce any allergic reactions upon contact with human skin. Likewise, the products have toxicologically favorable values and exhibit no bacteria-inhibiting properties with respect to waste water bacteria in the sewage system. Given a utilization of the surface-active substances, the method products, over and above this, are also completely biologically degradable; indeed they have considerably shorter degradable time spans than is typically the case.

It is also possible to add additives for the manufacture of cleaning agents and detergents such as oils, fats and waxes, mineral adjuvants as well as herbs or herb extracts to the product.

EXAMPLE 3

In combination with suitable surface-active substances such as, for example, fatty alcohol sulphates, fatty alcohol ether sulfates, fatty alcohol polyglycol ethers on the basis of linear, vegetable fats and oils, protein fatty acid condensates, coco-betaines, etc., as well as oils and fats for re-fatting, the whey manufactured according to the method of the present invention can also be utilized as a body cleaning agent. For example, the whey can be utilized in the form of washing lotions, showers, bubble baths, etc.

The use of *Lactobacillus acidophilus* for the modification of the whey is particularly suitable for this application. This is due to the fact that the a milieu that is thereby formed, is particularly gentle to the skin, mucous membranes and body. By setting the pH value appropriately, the natural whey complex with its proteins, vitamins, amino acids, and trace elements has an optimum coincidence with the natural dermic acid protection of the human skin.

EXAMPLE 4

The whey manufactured according to the method of the present invention can also be used as an aqueous basis for the manufacture of creams, lotions, salves, or masks. To this end, mineral, animal and/or vegetable fats or oils are mixed with an emulsifier and the modified whey is worked into the heated mixture. Processing without heating by utilizing a corresponding cold emulsifier is also possible. If desired, the resultant emulsions can be perfumed, provided with additional active ingredients and, if necessary and desired, can be preserved.

By utilizing a suitable lactic acid bacteria such as, for example, *Lactobacillus acidophilus,* it has been found that the inventively manufactured products are especially well-suited for body care, due to their special affinity to the human skin. Due to the biologically produced whey complex, the products protect and promote the natural skin milieu and, thus, the biological protective mechanisms of the skin. The products manufactured based on the whey manufactured pursuant to the method of the present invention, like the modified whey itself, have at least 60% of the natural moisture retaining factors of the human skin in the form of lactates, proteins, trace elements, and amino acids. Over and above this, the cosmetic products manufactured upon use of the modified whey have a natural lactic acid milieu that is closely related to the human skin.

EXAMPLE 5

The whey manufactured according to the method of the present invention can also be utilized for the manufacture of pharmaceutical preparations for improving, maintaining, and/or restoring the immune system of the human skin and mucous membrane. The milieu present in the inventively manufactured whey that ensues with and is controlled by the use of *Lactobacillus acidophilus* is identical, for example, to the natural lactic acid milieu in the female vaginal flora and guarantees an inflammation-inhibiting and infection-inhibiting protection there.

It has been shown that an improvement of inflammatory disease conditions such as, for example, fluoralbus can be achieved with the inventively modified whey or preparations manufactured therewith, by restoring the natural lactic acid milieu. Inflamed skin can also be treated by applying the inventively modified whey.

The above effects can be further enhanced by adding vegetable, inflammation-inhibiting ingredients such as, for example, camomile. Either alone or in combination with, for example, camomile, the inventively modified whey can also be employed as a medicinal bath additive.

EXAMPLE 6

Camomile blossoms are added to the whey before inoculation with lactic acid bacteria. The entire mixture is then subjected to anaerobic fermentation. A fermentation extract of whey and camomile blossoms produced in this manner has a higher effective use as a tincture for skin inflammations and inflammatory skin conditions. The special effect of medicinal herbs such as camomile blossoms in this case is apparently intensified by the simultaneous, anaerobic fermentation with the whey and is supplemented and optimized by the biological activity and by the physiological properties of the fermented whey.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A process for the manufacture of modified whey utilizing lactic acid bacteria, for use in the manufacture of washing-active substances, cosmetics, and pharmaceutical products, comprising the step of at least partially freeing the whey of lactose by utilizing a suitable lactic acid bacteria on the basis of fermentation, and further including the step of adding to the whey at least one component chosen from the group consisting of medicinal herbs, vegetable ingredients, and extracts thereof before the fermentation step.

2. The process of claim 1 including the step of inoculating the whey with at least one lactic acid bacterium phylum before the fermentation.

3. The process of claim 1 including the step of inoculating the whey with at least one lactic acid bacterium phylum during the fermentation.

4. The process of claim 1 wherein the lactic acid bacteria is chosen from the group consisting of *Lactobacillus acidophilus, Lactobacillus bulgaris, Lactobacillus lactis, Lactobacillus helveticus, Lactobacillus casei, Streptococcus lactis* and *Streptococcus thermophilus.*

5. The process of claim 1 wherein the duration of the fermentation process is controlled so that the lactose is almost completely broken down.

6. The process of claim 1 including the step of drying the resultant modified whey.

7. The process of claim 1 including the step of vacuum drying the resultant modified whey.

8. The process of claim 1 including the step of freeze drying the modified whey.

9. The process of claim 1 including the step of drawing off the modified whey under $CO_2$ excess.

10. The process of the process of claim 1.

11. The product of the process of claim 1.

* * * * *